(12) United States Patent
Chang

(10) Patent No.: US 11,875,508 B2
(45) Date of Patent: Jan. 16, 2024

(54) TRANSMISSIVE LIGHT BASED TREMOR IDENTIFICATION METHOD AND SYSTEM THEREOF

(71) Applicant: National Central University, Taoyuan (TW)

(72) Inventor: Rong-Seng Chang, Taipei (TW)

(73) Assignee: National Central University, Taoyuan (TW)

( * ) Notice: Subject to any disclaimer, the term of this patent is extended or adjusted under 35 U.S.C. 154(b) by 403 days.

(21) Appl. No.: 16/996,837

(22) Filed: Aug. 18, 2020

(65) Prior Publication Data

US 2021/0056698 A1 Feb. 25, 2021

(30) Foreign Application Priority Data

Aug. 19, 2019 (TW) ................................ 108129443

(51) Int. Cl.
*G06T 7/00* (2017.01)
*G06T 7/262* (2017.01)
(Continued)

(52) U.S. Cl.
CPC .......... *G06T 7/0014* (2013.01); *A61B 5/0077* (2013.01); *A61B 5/1101* (2013.01); *A61B 5/1128* (2013.01); *A61B 5/4082* (2013.01); *A61B 5/441* (2013.01); *A61B 5/489* (2013.01); *A61B 5/4893* (2013.01); *A61B 5/7267* (2013.01); *A61B 6/5247* (2013.01);
(Continued)

(58) Field of Classification Search
CPC ....... G06T 7/0014; G06T 7/262; G06T 7/246; G06N 20/00; A61B 5/0077; A61B 5/1101; A61B 5/1128

USPC ......................................................... 382/128
See application file for complete search history.

(56) References Cited

U.S. PATENT DOCUMENTS 9,683,837 B2 * 6/2017 Siercks ................. G01B 11/25
2018/0153422 A1 6/2018 Watanabe
(Continued)

FOREIGN PATENT DOCUMENTS

CN 105701806 6/2016
TW M591390 3/2020

OTHER PUBLICATIONS

Chang et al., A Parkinson's Disease Measurement System Using Laser Lines and a CMOS Image Sensor, 2011, Sensor. (Year: 2011).*

(Continued)

*Primary Examiner* — Wednel Cadeau
(74) *Attorney, Agent, or Firm* — JCIPRNET

(57) ABSTRACT

The disclosure provides a transmissive light based tremor identification method and a system thereof. The method includes: projecting, with a transmissive light, a first optical pattern to a part to be measured, wherein the transmissive light penetrates a surface of the part to be measured and correspondingly forms a second optical pattern on an internal structure of the part to be measured, and the second optical pattern is synthesized to include at least one intersection; capturing a plurality of images of the second optical pattern on the internal structure of the part to be measured and acquiring a motion feature of each intersection based on the images; and identifying a tremor pattern of the internal structure of the part to be measured based on the motion feature of each intersection.

13 Claims, 3 Drawing Sheets

(51) Int. Cl.
*G06T 7/246* (2017.01)
*G06N 20/00* (2019.01)
*A61B 5/11* (2006.01)
*A61B 5/00* (2006.01)
*A61B 6/00* (2006.01)
*H04N 9/31* (2006.01)

(52) U.S. Cl.
CPC ............ *G06N 20/00* (2019.01); *G06T 7/246* (2017.01); *G06T 7/262* (2017.01); *H04N 9/31* (2013.01); *A61B 2503/40* (2013.01); *G06T 2207/10048* (2013.01); *G06T 2207/10116* (2013.01); *G06T 2207/20081* (2013.01); *G06T 2207/30004* (2013.01)

(56) References Cited

U.S. PATENT DOCUMENTS

2020/0281477 A1* 9/2020 Islam .................... G01N 33/025
2020/0364868 A1* 11/2020 Zhang .................... G06T 7/248

OTHER PUBLICATIONS

Chang et al., Application of Automatized 3D Moire Monitoring System in Pulse Measurement, 2015, Optics Express. (Year: 2015).*

* cited by examiner

TRANSMISSIVE LIGHT BASED TREMOR IDENTIFICATION METHOD AND SYSTEM THEREOF

CROSS-REFERENCE TO RELATED APPLICATION

This application claims the priority benefit of Taiwan application serial no. 108129443, filed on Aug. 19, 2019. The entirety of the above-mentioned patent application is hereby incorporated by reference herein and made a part of this specification.

BACKGROUND

Technical Field

The disclosure relates to an identification method and a system thereof, and more particularly to a transmissive light based tremor identification method and a system thereof.

Description of Related Art

Parkinson's disease (PD) is a common degenerative disease of the nervous system, the clinical manifestations thereof include resting tremor, bradykinesia, myotonia, and postural gait disorder, and patients may be simultaneously accompanied by non-motor symptoms such as depression, constipation, and sleep disorder. In the above clinical manifestations, resting tremor is the most common symptom, but it is more difficult to visually observe the relevant tremor situation.

Most of the relevant researches of PD are carried out based on high-efficiency medical images such as magnetic resonance imaging (MRI), single photon emission computed tomography (SPECT), positron emission tomography (PET), etc. However, since the above medical images are not only more costly to use, but will also produce relevant radiation problems, they are more difficult to be configured as means for daily tracking and evaluation of therapeutic effects.

SUMMARY

In view of the above, the disclosure provides a transmissive light based tremor identification method and a system thereof, which can be configured to solve the above technical problems.

The disclosure provides a transmissive light based tremor identification method including the following steps. A first optical pattern is projected with a transmissive light to a part to be measured, wherein the transmissive light penetrates a surface of the part to be measured and correspondingly forms a second optical pattern on an internal structure of the part to be measured, and the second optical pattern is synthesized to include at least one intersection. A plurality of images of the second optical pattern on the internal structure of the part to be measured are captured and a motion feature of each intersection is acquired based on the images. A tremor pattern of the internal structure of the part to be measured is identified based on the motion feature of each intersection.

The disclosure relates to a tremor identification system, including a projection device, an image capturing device, and a processing device. The processing device is coupled between the image capturing device and the projection device, and is configured to: control the projection device to project, with a transmissive light, a first optical pattern to a part to be measured, wherein the transmissive light penetrates a surface of the part to be measured and correspondingly forms a second optical pattern on the part to be measured, and the second optical pattern is synthesized to include at least one intersection; control the image capturing device to capture a plurality of images of the second optical pattern on the internal structure of the part to be measured and acquire a motion feature of each intersection based on the images; and identify a tremor pattern of the internal structure of the part to be measured based on the motion feature of each intersection.

Based on the above, the transmissive light based tremor identification method and the system thereof according to the disclosure can identify the tremor pattern of the internal structure of the part to be measured based on the motion feature of the intersection in the second optical pattern projected to the internal structure of the part to be measured. As such, an instant, low-cost, non-intrusive tremor identification mechanism can be provided.

To make the aforementioned and other features of the disclosure more comprehensible, several embodiments accompanied with drawings are described in detail as follows.

DETAILED DESCRIPTION OF DISCLOSED EMBODIMENTS

Roughly speaking, the disclosure can observe a motion feature presented by an intersection on a second optical pattern following a movement of an internal structure of a part to be measured and identify a tremor pattern of the internal structure of the part to be measured by an artificial intelligence model after a first optical pattern having the intersection is projected with a transmissive light to the internal structure of the part to be measured to form the second optical pattern on the internal structure of the part to be measured. In the relevant applications, since the tremor pattern appearing in patients with Parkinson's disease (PD) will be different from patients without PD, the artificial intelligence model may identify an unknown patient as a PD patient or non-PD patient based on the tremor pattern of the unknown patient after the artificial intelligence model is trained with the tremor patterns of PD patients and non-PD patients. Further explanation will be given below.

Figure 1:
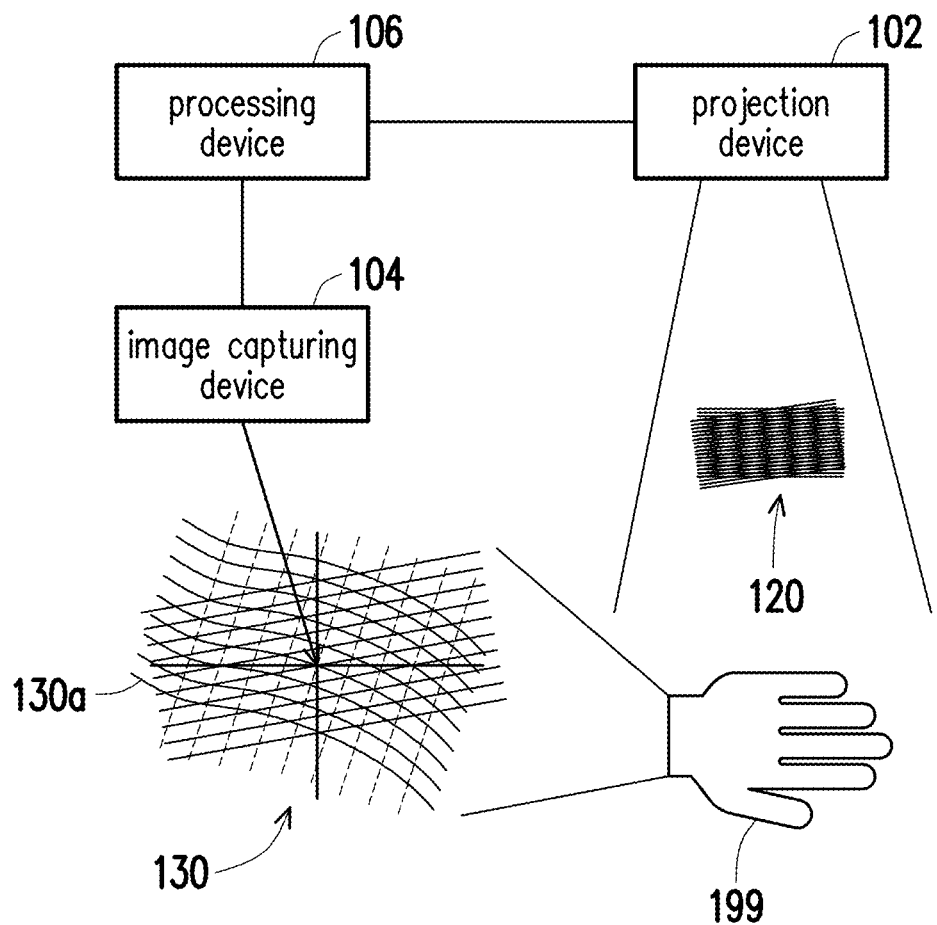
FIG. 1 is a schematic view of identifying a tremor pattern of an internal structure of a part to be measured according to an embodiment of the disclosure.

Please refer to FIG. 1, which is a schematic view of identifying a tremor pattern of a part to be measured according to an embodiment of the disclosure. In FIG. 1, a tremor identification system 100 includes a projection device 102, an image capturing device 104, and a processing device 106. In different embodiments, the projection device 102 is, for example, a digital light processing (DLP) projector or other similar projection devices, and may be controlled by the processing device 106 to project with a transmissive light a designated pattern to a designated object. In different embodiments, the transmissive light is, for example, an infrared, an X-ray, or other light which may be configured to penetrate objects, but is not limited thereto.

Taking FIG. 1 as an example, the projection device 102 may be controlled by the processing device 106 to project with a transmissive light a first optical pattern 120 to a part to be measured 199 (for example, a hand). In the embodiment, the first optical pattern 120 is, for example, a moiré pattern, but the disclosure is not limited thereto. In other embodiments, the projection device 102 may also project a pattern having another pattern as the first optical pattern 120 as long as the pattern has at least one intersection. In other embodiments, a pattern without any intersection, for example, a plurality of parallel lines, etc., may also be adopted as the first optical pattern 120, but is not limited thereto.

The image capturing device 104 is, for example, any camera having a charge coupled device (CCD) lens, a complementary metal oxide semiconductor transistors (CMOS) lens, or a camera capable of detecting transmissive light, for example, an infrared camera, an X-ray camera, etc., but the disclosure is not limited thereto.

In the embodiment, when the first optical pattern 120 is projected with a transmissive light to the part to be measured 199, the transmissive light may penetrate a surface of the part to be measured 199 and correspondingly form a second optical pattern 130 on an internal structure of the part to be measured 199. In different embodiments, the internal structure may be at least one of dermal, vascular, nerve, and fascial interstitial tissues or any tissue in the human body, but the disclosure is not limited thereto.

In an embodiment, the first optical pattern 120 is deformed in response to the contour of the internal structure of the part to be measured 199, thereby forming a second optical pattern 130 on the internal structure of the part to be measured 199. Under such situation, the image capturing device 104 may be controlled by the processing device 106 to continuously capture a plurality of images of the second optical pattern 130.

In FIG. 1, since one or more intersections may be included in the first optical pattern 120, after the first optical pattern 120 is projected to the internal structure of the part to be measured 199, the second optical pattern 130 is also correspondingly synthesized to include one or more intersections (for example, an intersection 130a as shown in FIG. 1). In detail, after the first optical pattern 120 is projected to the internal structure of the part to be measured 199, a shadow may be formed on the internal structure of the part to be measured 199, and the shadow may overlap and interfere with the first optical pattern 120, thereby producing the second optical pattern 130 (which is presented as for example, a contour line pattern).

Under such situation, if a tremor appears in the internal structure of the part to be measured 199, the position of each intersection on the second optical pattern 130 in the images will be changed. Therefore, the tremor of the internal structure of the part to be measured 199 may be correspondingly derived by tracking the positional change of each intersection on the second optical pattern 130 in the images, but the disclosure is not limited thereto.

In addition, in other embodiments, if the first optical pattern is implemented as a pattern without any intersection (for example, one or more parallel lines), after the first optical pattern is projected to the internal structure of the part to be measured 199, another type of shadow (for example, one or more parallel lines) is formed on the internal structure of the part to be measured 199, and the shadow may overlap and interfere with the first optical pattern to produce a second optical pattern, but the disclosure is not limited thereto.

The processing device 106 is coupled to the projection device 102 and the image capturing device 104, and may be a mobile phone, a smart phone, a personal computer (PC), a notebook PC, a netbook PC, or a tablet PC, but the disclosure is not limited thereto. It should be understood that although the projection device 102, the image capturing device 104, and the processing device 106 are illustrated as three different devices in FIG. 1, in other embodiments, the three devices may also be integrated as one single device.

Figure 2:
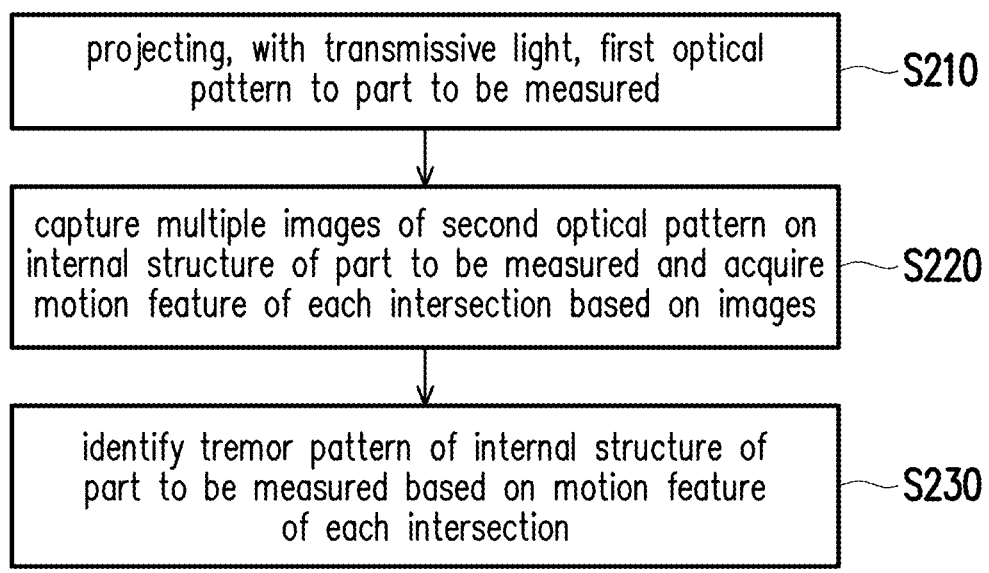
FIG. 2 is a flowchart of a transmissive light based tremor identification method according to an embodiment of the disclosure.

Please refer to FIG. 2, which is a flowchart of a transmissive light based tremor identification method according to an embodiment of the disclosure. The method of the embodiment may be executed by the tremor identification system 100 of FIG. 1. The details of each step of FIG. 2 will be described below with the elements shown in FIG. 1.

First, in Step S210, the processing device 106 may control the projection device 102 to project with a transmissive light the first optical pattern 120 to the part to be measured 199, wherein the transmissive light penetrates a surface of the part to be measured 199 and correspondingly forms the second optical pattern 130 on the internal structure of the part to be measured 199. As described in the previous embodiment, under the situation where the first optical pattern 120 includes at least one intersection, the second optical pattern 130 formed on the internal structure of the part to be measured 199 will also include at least one intersection (for example, the intersection 130a). In the embodiment, the part to be measured 199 is, for example, a hand of an unknown patient, but is not limited thereto.

Next, in Step S220, the processing device 106 may control the image capturing device 104 to capture a plurality of images of the internal structure of the second optical pattern 130 on the part to be measured 199 and acquire a motion feature of each intersection based on the images.

In different embodiments, the motion feature of each intersection may be characterized as the amplitude, shape, tremor frequency, etc. of each intersection, but the disclosure is not limited thereto. For ease of explanation, the following description will be made only based on the intersection 130a in the second optical pattern 130, and persons of ordinary skill in the art should be able to derive the operation of the processing device 106 based on other intersections in the second optical pattern 130 according to the relevant teachings.

In an embodiment, the processing device 106 may acquire the tremor frequency of the intersection 130a in the images captured by the image capturing device 104 based on a fast Fourier transform (FFT). In another embodiment, the processing device 106 may acquire a plurality of positions of the intersection 130a in the images and obtain the amplitude of the intersection 130a, which is the movement range of the intersection 130a in the images, by analyzing the change of the positions.

In addition, in other embodiments, the images are, for example, a plurality of infrared images captured by the infrared camera. Under such situation, the processing device 106 may acquire a grayscale value change of the intersection 130a in the infrared images and obtain the amplitude of the intersection 130a by analyzing the grayscale value change, but is not limited thereto.

Thereafter, in Step S230, the processing device 106 may identify the tremor pattern of the internal structure of the part to be measured 199 based on the motion feature of each intersection. In an embodiment, the processing device 106 may input the motion feature of each intersection into the artificial intelligence model to identify whether the tremor pattern of the internal structure of the part to be measured 199 belongs to a first type tremor or a second type tremor.

In order for the artificial intelligence model to be able to identify the tremor pattern of the internal structure of the part to be measured 199, the processing device 106 may train the artificial intelligence model in advance with a plurality of training images, wherein the training images include a plurality of first type images and a plurality of second type images, wherein the first type images correspond to the first type tremor and the second type images correspond to the second type tremor.

In one embodiment, if it is desired for the artificial intelligence model to be able to identify PD, then the first type images may be captured from one or more first patients with PD and the second type images may be captured from one or more second patients without PD. For example, if the part to be measured 199 is a hand of an unknown patient, then the first type images may be an internal structure image of a hand of each first patient and the second type images may be a hand image of each second patient. Under such situation, the artificial intelligence model may learn the tremor pattern (i.e. the first type tremor) of internal structures of hands of first patients with PD from the first type images and learn the tremor pattern (i.e. a second type tremor) of internal structures of hands of second patients without PD from the second type images.

Moreover, in the training stage of the artificial intelligence model, the processing device 106 may control the projection device 102 to project with a transmissive light the first optical pattern 120 to a first predetermined part of the first patient (i.e. the PD patient), wherein the transmissive light penetrates a surface of the first predetermined part and correspondingly forms a third optical pattern (i.e. the first optical pattern 120 which deforms following the contour of the first predetermined part) on a first internal structure of the first predetermined part. In the embodiment, the third optical pattern includes at least one first intersection and the first predetermined part corresponds to the part to be measured (for example, both are hands). Thereafter, the processing device 106 may control the image capturing device 104 to capture images of the third optical pattern on the first internal structure of the first predetermined part as the first type images and acquire the tremor frequency of each first intersection based on the first type images captured. Thereafter, the processing device 106 may acquire the frequency peak value of the tremor frequency of each first intersection, and map each first intersection and the corresponding frequency peak value to a first standard part diagram to produce a first tremor distribution diagram. Next, the processing device 106 may mark the first tremor distribution diagram as the first type tremor and feed into the artificial intelligence model for the artificial intelligence model to learn the features of the first type tremor.

Similarly, the processing device 106 may control the projection device 102 to project with a transmissive light the first optical pattern 120 to a second predetermined part of the second patient (i.e. the non-PD patient), wherein the transmissive light penetrates a surface of the second predetermined part and correspondingly forms a fourth optical pattern (i.e. the first optical pattern 120 which deforms following the contour of the second predetermined part) on a second internal structure of the second predetermined part. In the embodiment, the fourth optical pattern includes at least one second intersection and the second predetermined part corresponds to the part to be measured (for example, both are hands). Thereafter, the processing device 106 may control the image capturing device 104 to take images of the fourth optical pattern on the second internal structure of the second predetermined part as the second type images and acquire the tremor frequency of each second intersection based on the second type images captured. Thereafter, the processing device 106 may acquire the frequency peak value of the tremor frequency of each second intersection, and map each second intersection and the corresponding frequency peak value to a second standard part diagram to produce a second tremor distribution diagram. Next, the processing device 106 may mark the second tremor distribution diagram as the second type tremor and feed into the artificial intelligence model for the artificial intelligence model to learn the features of the second type tremor.

Figure 3:
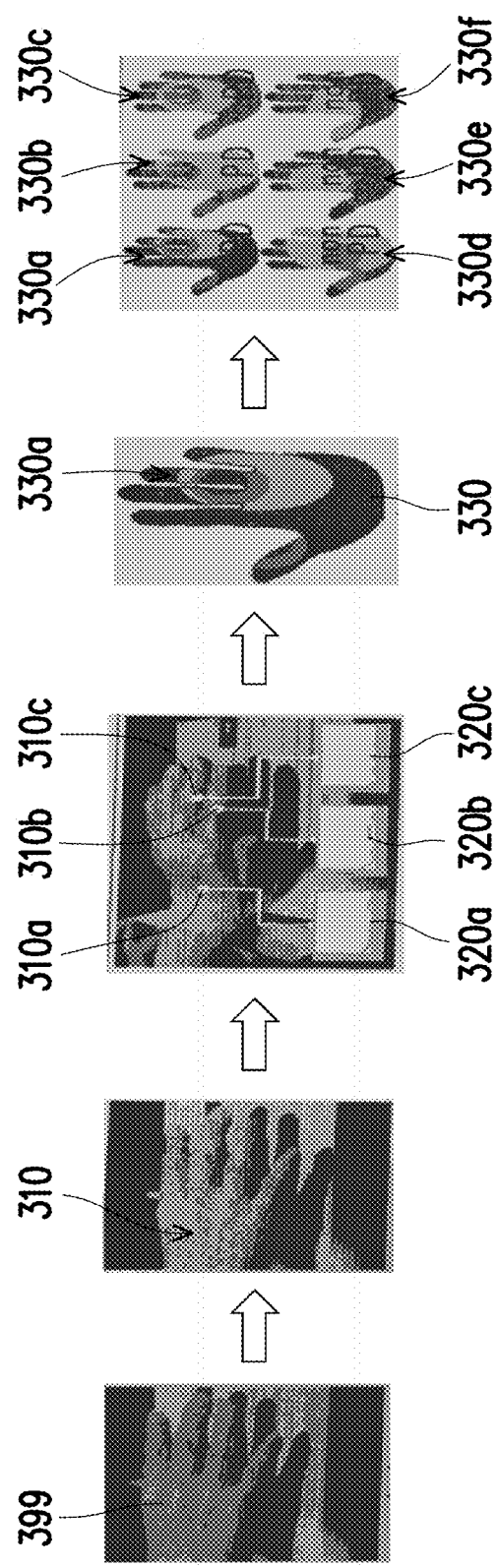
FIG. 3 is a schematic view of marking training data according to an embodiment of the disclosure.

In order to make the above concept clearer, the following description is supplemented using FIG. 3. Please refer to FIG. 3, which is a schematic view of marking training data according to an embodiment of the disclosure. In the embodiment, it is assumed that a PD patient places a first predetermined part 399 (i.e. a hand) thereof under a projection device (not shown) of the disclosure and the processing device (not shown) of the disclosure may correspondingly control the projection device to project with a transmissive light a first optical pattern to the first predetermined part 399, so as to form a third optical pattern 310 on the first internal structure of the first predetermined part 399. Thereafter, the processing device may acquire a motion feature of each first intersection on the third optical pattern 310 based on a plurality of first type images of the first internal structure of the first predetermined part 399 captured by an image capturing device (not shown). Taking first intersections 310*a*, 310*b*, and 310*c* on the third optical pattern 310 as examples, the processing device may characterize the motion features of the first intersections 310*a* to 310*c* as the tremor frequency of each first intersection 310*a* to 310*c*.

In FIG. 3, diagrams 320*a*, 320*b*, and 320*c* may respectively be tremor frequency distribution diagrams of the first intersections 310*a* to 310*c* acquired by the FFT, but the disclosure is not limited thereto.

Thereafter, the processing device may acquire the frequency peak value of the tremor frequency of each first intersection, and map each first intersection and the frequency peak value thereof to a first standard part diagram 330 to produce a first tremor distribution diagram 330*a*, wherein the first intersection with a different frequency peak value may be labeled with a different color. Thereafter, the processing device may mark the first tremor distribution diagram 330*a* as a first type tremor (i.e. tremor of a PD patient) and feed into the artificial intelligence model for the artificial intelligence model to learn the features of the first type tremor.

Similarly, the tremor identification system of the disclosure may also carry out the above operation on other first patients (for example, PD patients) to produce first tremor distribution diagrams 330*b* and 330*c*. Thereafter, the tremor identification system of the disclosure may mark the first tremor distribution diagrams 330*b* and 330*c* as the first type tremor (i.e. tremor of PD patients), and feed into the artificial intelligence model for the artificial intelligence model to learn the features of the first type tremor.

In addition, the tremor identification system of the disclosure may also perform the above operation on other second patients (for example, non-PD patients) to produce second tremor distribution diagrams 330*d*, 330*e*, and 330*f*. Thereafter, the tremor identification system of the disclosure may mark the second tremor distribution diagrams 330*d*, 330e, and 330f as a second type tremor (i.e. tremor of non-PD patients), and feed into the artificial intelligence model for the artificial intelligence model to learn the features of the second type tremor.

After completing the training of the artificial intelligence model, the processing device 106 may input the motion feature (for example, amplitude, tremor frequency, etc.) of each intersection into the artificial intelligence model. For example, the processing device 106 may also map the frequency peak value of each intersection and the tremor frequency thereof to a standard part diagram which may be fed into the artificial intelligence model, so as to form the tremor distribution diagram corresponding to the internal structure of the part to be measured 199 on the standard part diagram.

Thereafter, the artificial intelligence model may identify whether the tremor pattern of the internal structure of the part to be measured 199 (i.e. the hand of an unknown patient) belongs to the first type tremor or the second type tremor. If the tremor pattern of the internal structure of the part to be measured 199 belongs to the first type tremor, it represents that the unknown patient may have PD. Conversely, if the tremor pattern of the internal structure of the part to be measured 199 belongs to the second type tremor, it represents that the unknown patient may not have PD.

In short, after training the artificial intelligence model with the tremor patterns of internal structures of hands of PD patients and non-PD patients as the training data, the artificial intelligence model may identify whether an unknown patient has PD based on the tremor pattern of the internal structure of the hand of the unknown patient, but the disclosure is not limited thereto. In other embodiments, the processing device 106 may also train the artificial intelligence model based on tremor patterns of internal structures of other parts of PD patients and non-PD patients without being limited to the hand in the above embodiments.

In some embodiments, the concept of the disclosure is applicable to identifying tremor patterns of internal structures of other forms of parts to be measured. For example, plants, animals other than human, minerals, etc. may all be considered by the disclosure as parts to be measured. Under such situation, the system of the disclosure may correspondingly train the artificial intelligence model to allow the artificial intelligence model to be able to identify the tremor patterns of internal structures of plants, animals, and minerals. Refer to the descriptions in the previous embodiments for details, which will not be reiterated herein.

Based on the above, the transmissive light based tremor identification method and the system thereof provided by the disclosure can observe the motion feature of the intersection on the second optical pattern after projecting with a transmissive light the first optical pattern having the intersection to the part to be measured, so as to form the second optical pattern on the internal structure of the part to be measured and identify whether the tremor pattern of the internal structure of the part to be measured belongs to the first type tremor or the second type tremor by the artificial intelligence model. As such, an instant, low-cost, non-intrusive, and non-contact tremor identification mechanism can be provided. Moreover, through proper training of the artificial intelligence model, the artificial intelligence model is able to identify specific diseases (for example, PD), so as to be effectively used as means for daily tracking and evaluation of therapeutic effects. Moreover, the method provided by the disclosure may also assist doctors to make relevant diagnosis when tremor of a PD patient is not yet obvious, so that relevant medical staff may adopt corresponding treatment means, thereby facilitating the control of the disease.

Furthermore, for patients with typical PD (i.e. tremor is visible to the naked eye) or atypical PD (i.e. tremor is not visible to the naked eye), the disclosure may be configured to assist in identifying the tremor pattern of the internal structure of the part to be measured. Furthermore, even if the tremor situation of a patient is slowed down after taking medication, the remaining minor tremor pattern after the improvement may still be observed by the method and the system thereof of the disclosure, thereby assisting doctors to make relevant diagnosis.

Moreover, the disclosure may also be used to identify the tremor patterns of the internal structures of various parts to be measured, such as plants, animals, minerals, etc., and thus may be configured to assist relevant researchers to research on the parts to be measured.

Although the disclosure has been disclosed in the above embodiments, the embodiments are not intended to limit the disclosure. It will be apparent to persons skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A transmissive light based tremor identification method, comprising:
projecting, with a transmissive light, a first optical pattern to a part to be measured, wherein the transmissive light penetrates a surface of the part to be measured and forms a shadow, and the shadow and the first optical pattern correspondingly forms a second optical pattern on an internal structure of the part to be measured, and the second optical pattern is synthesized to comprise at least one intersection by a processing device;
capturing a plurality of images of the second optical pattern on the internal structure of the part to be measured and acquiring a motion feature of each intersection based on the position changes of the intersection as represented in plurality of images by the processing device; and
identifying a tremor pattern of the internal structure of the part to be measured based on the motion feature each of the intersection by the processing device, wherein the step comprises:
inputting the motion feature of each of the intersection into an artificial intelligence model, so that the artificial intelligence model identifies whether the tremor pattern of the internal structure of the part to be measured belongs to a first type tremor or a second type tremor, further comprising:
training the artificial intelligence model by a plurality of training images, wherein the plurality of training images comprise a plurality of first type images and a plurality of second type images, wherein the plurality of first type images correspond to the first type tremor and the plurality of second type images correspond to the second type tremor.

2. The method according to claim 1, wherein the first optical pattern is a moiré pattern.

3. The method according to claim 1, wherein the motion feature of each of the intersection comprises a tremor frequency of each of the intersection and the step of acquiring the motion feature of each of the intersection based on the plurality of images comprises:

acquiring the tremor frequency of a first intersection in the plurality of images based on a fast Fourier transform for the first intersection in the at least one intersection.

4. The method according to claim 1, wherein the motion feature of each of the intersection comprises an amplitude of each of the intersection and the step of acquiring the motion feature of each of the intersection based on the plurality of images comprises:
   acquiring a plurality of positions of a first intersection in the plurality of images for the first intersection in the at least one intersection; and
   analyzing a change of the plurality of positions to obtain the amplitude of the first intersection.

5. The method according to claim 1, wherein the plurality of images comprise a plurality of infrared images, the motion feature of each of the intersection comprises an amplitude of each of the intersection, and the step of acquiring the motion feature of each of the intersection based on the plurality of images comprises:
   acquiring a grayscale value change of a first intersection in the plurality of infrared images for the first intersection in the at least one intersection; and
   analyzing the grayscale value change to obtain the amplitude of the first intersection.

6. The method according to claim 1, wherein the plurality of first type images are captured from a first patient with Parkinson's disease and the plurality of second type images are captured from a second patient without Parkinson's disease.

7. The method according to claim 1, wherein the part to be measured is a hand of an unknown patient.

8. The method according to claim 1, wherein the internal structure comprises at least one of dermal, vascular, nerve, and fascial interstitial tissues.

9. The method according to claim 1, wherein the part to be measured comprises at least one of a plant, an animal, and a mineral.

10. The method according to claim 1, wherein the transmissive light comprises at least one of an infrared and an X-ray.

11. The method according to claim 6, further comprising:
   projecting, with a transmissive light, the first optical pattern to a first predetermined part of the first patient, wherein the transmissive light penetrates a surface of the first predetermined part and correspondingly forms a third optical pattern on a first internal structure of the first predetermined part, wherein the third optical pattern comprises at least one first intersection and the first predetermined part corresponds to the part to be measured;
   capturing the plurality of first type images of the third optical pattern on the first internal structure of the first predetermined part and acquiring a tremor frequency of each of the first intersection based on the plurality of first type images;
   acquiring a frequency peak value of the tremor frequency of each of the first intersection;
   mapping each of the first intersection and a corresponding frequency peak value to a first standard part diagram to produce a first tremor distribution diagram; and
   marking the first tremor distribution diagram as the first type tremor and feeding into the artificial intelligence model for the artificial intelligence model to learn features of the first type tremor.

12. The method according to claim 11, further comprising:
   projecting, with a transmissive light, the first optical pattern to a second predetermined part of the second patient, wherein the transmissive light penetrates a surface of the second predetermined part and correspondingly forms a fourth optical pattern on a second internal structure of the second predetermined part, wherein the fourth optical pattern comprises at least one second intersection and the second predetermined part corresponds to the part to be measured;
   capturing the plurality of second type images of the fourth optical pattern on the second internal structure of the second predetermined part and acquiring a tremor frequency of each of the second intersection based on the plurality of second type images;
   acquiring a frequency peak value of the tremor frequency of each of the second intersection; and
   mapping each of the second intersection and a corresponding frequency value to a second standard part diagram to produce a second tremor distribution diagram; and
   marking the second tremor distribution diagram as the second type tremor and feeding into the artificial intelligence model for the artificial intelligence model to learn features of the second type tremor.

13. A tremor identification system, comprising:
   a projection device;
   an image capturing device;
   a processing device, coupled to the image capturing device and the projection device, and configured to:
   control the projection device to project with a transmissive light a first optical pattern to a part to be measured, wherein the transmissive light penetrates a surface of the part to be measured and forms a shadow, and the shadow and the first optical pattern correspondingly forms a second optical pattern on an internal structure of the part to be measured, and the second optical pattern is synthesized to comprise at least one intersection;
   control the image capturing device to capture a plurality of images of the second optical pattern on the internal structure of the part to be measured and acquire a motion feature of each of the intersection based on the plurality of images; and
   identify a tremor pattern of the internal structure of the part to be measured based on the motion feature of each of the intersection, wherein the step comprises:
   inputting the motion feature of each of the intersection into an artificial intelligence model, so that the artificial intelligence model identifies whether the tremor pattern of the internal structure of the part to be measured belongs to a first type tremor or a second type tremor, further comprising:
   training the artificial intelligence model by a plurality of training images, wherein the plurality of training images comprise a plurality of first type images and a plurality of second type images, wherein the plurality of first type images correspond to the first type tremor and the plurality of second type images correspond to the second type tremor.

* * * * *